United States Patent
Potts et al.

(10) Patent No.: US 12,337,173 B2
(45) Date of Patent: Jun. 24, 2025

(54) DEVICES, SYSTEMS, AND METHODS FOR PROMOTING VOIDING IN SUBJECTS WITH UNDERACTIVE BLADDERS

(71) Applicants: Duke University, Durham, NC (US); THE UNITED STATES GOVERNMENT AS REPRESENTED BY THE DEPARTMENT OF VETERANS AFFAIRS, Washington, DC (US)

(72) Inventors: Bradley Potts, Durham, NC (US); Matthew Fraser, Durham, NC (US)

(73) Assignees: Duke University, Durham, NC (US); The United States Government as Represented by the Department of Veterans Affairs, Washington, DC (US)

( * ) Notice: Subject to any disclaimer, the term of this patent is extended or adjusted under 35 U.S.C. 154(b) by 307 days.

(21) Appl. No.: 17/631,208

(22) PCT Filed: Jul. 30, 2020

(86) PCT No.: PCT/US2020/044218
§ 371 (c)(1),
(2) Date: Jan. 28, 2022

(87) PCT Pub. No.: WO2021/022020
PCT Pub. Date: Feb. 4, 2021

(65) Prior Publication Data
US 2022/0266010 A1 Aug. 25, 2022

Related U.S. Application Data

(60) Provisional application No. 62/880,239, filed on Jul. 30, 2019.

(51) Int. Cl.
*A61N 1/36* (2006.01)
*A61N 1/05* (2006.01)

(52) U.S. Cl.
CPC ....... *A61N 1/36007* (2013.01); *A61N 1/0514* (2013.01); *A61N 1/0551* (2013.01);
(Continued)

(58) Field of Classification Search
CPC .............. A61N 1/36007; A61N 1/0514; A61N 1/0551; A61N 1/36153; A61N 1/36171; A61N 1/36178; A61N 1/3787
See application file for complete search history.

(56) References Cited

U.S. PATENT DOCUMENTS

| 4,739,764 A | 4/1988 | Lue et al. |
| 4,771,779 A | 9/1988 | Tanagho et al. |

(Continued)

FOREIGN PATENT DOCUMENTS

WO   WO 2023/064029 A1   4/2023

OTHER PUBLICATIONS

International Search Report and Written Opinion For PCT/US20/44218. Mailed Nov. 9, 2020. 12 pages.
(Continued)

*Primary Examiner* — John R Downey
(74) *Attorney, Agent, or Firm* — Casimir Jones, S.C.; Peter J. Schlueter

(57) ABSTRACT

This present disclosure provides devices, systems, and methods for the treatment of conditions pertaining to bladder control. In particular, the present disclosure provides devices, systems, and methods directed to the application of electrical stimulation to the proximal urethra and associated nervous tissue to elicit voiding contractions that normalize bladder function.

12 Claims, 5 Drawing Sheets

(52) U.S. Cl.
CPC ..... *A61N 1/36153* (2013.01); *A61N 1/36171* (2013.01); *A61N 1/36178* (2013.01)

(56) References Cited

U.S. PATENT DOCUMENTS

| | | | |
|---|---|---|---|
| 6,393,323 | B1 | 5/2002 | Sawan et al. |
| 6,449,512 | B1 | 9/2002 | Boveja |
| 6,862,480 | B2 | 3/2005 | Cohen et al. |
| 6,907,293 | B2 | 6/2005 | Grill et al. |
| 7,047,078 | B2 | 5/2006 | Boggs, II et al. |
| 7,142,925 | B1 | 11/2006 | Bhadra et al. |
| 7,177,703 | B2 | 2/2007 | Boveja et al. |
| 7,276,057 | B2 | 10/2007 | Gerber |
| 7,328,068 | B2 | 2/2008 | Spinelli et al. |
| 7,328,069 | B2 | 2/2008 | Gerber |
| 7,369,894 | B2 | 5/2008 | Gerber |
| 7,427,280 | B2 | 9/2008 | Gerber |
| 7,571,000 | B2 | 8/2009 | Boggs, II et al. |
| 7,763,034 | B2 | 7/2010 | Siegal et al. |
| 7,894,913 | B2 | 2/2011 | Boggs et al. |
| 8,052,730 | B2 | 11/2011 | Brown et al. |
| 8,396,555 | B2 | 3/2013 | Boggs et al. |
| 8,467,875 | B2 | 6/2013 | Bennett et al. |
| 8,588,917 | B2 | 11/2013 | Whitehurst et al. |
| 8,805,510 | B2 | 8/2014 | Chancellor et al. |
| 9,174,045 | B2 | 11/2015 | Simon et al. |
| 9,192,764 | B2 | 11/2015 | Rohrer et al. |
| 9,272,140 | B2 | 3/2016 | Gerber |
| 9,283,391 | B2 | 3/2016 | Ahmed |
| 9,393,411 | B2 | 7/2016 | Bhadra et al. |
| 9,539,433 | B1 | 1/2017 | Wirbisky et al. |
| 9,610,442 | B2 | 4/2017 | Yoo et al. |
| 9,623,243 | B2 | 4/2017 | Chancellor et al. |
| 9,782,583 | B2 | 10/2017 | Sharma |
| 10,046,164 | B2 | 8/2018 | Gerber |
| 10,220,205 | B2 | 3/2019 | Bhadra et al. |
| 10,549,087 | B2 | 2/2020 | Yoo et al. |
| 10,722,708 | B2 | 7/2020 | Grill et al. |
| 10,994,134 | B2 | 5/2021 | Thor |
| 11,045,650 | B2 | 6/2021 | Brink et al. |
| 11,097,122 | B2 | 8/2021 | Lu |
| 11,103,723 | B2 | 8/2021 | Deisseroth et al. |
| 11,116,980 | B2 | 9/2021 | Nelson et al. |
| 11,278,721 | B2 | 3/2022 | Grill et al. |
| 11,672,978 | B2 | 6/2023 | Su et al. |
| 11,752,334 | B2 | 9/2023 | Yoo et al. |
| 2003/0018365 | A1 | 1/2003 | Loeb |
| 2004/0049240 | A1 | 3/2004 | Gerber |
| 2004/0193228 | A1 | 9/2004 | Gerber |
| 2005/0010260 | A1 | 1/2005 | Gerber |
| 2005/0020970 | A1 | 1/2005 | Gerber |
| 2005/0033373 | A1 | 2/2005 | Gerber |
| 2005/0033374 | A1 | 2/2005 | Gerber |
| 2005/0060005 | A1* | 3/2005 | Boggs, II ........... A61N 1/36196 607/40 |
| 2005/0070969 | A1 | 3/2005 | Gerber |
| 2005/0113878 | A1 | 5/2005 | Gerber |
| 2005/0143783 | A1* | 6/2005 | Boveja ............... A61N 1/36007 607/40 |
| 2007/0255333 | A1 | 11/2007 | Giftakis et al. |
| 2008/0071321 | A1* | 3/2008 | Boggs, II ........... A61N 1/36007 607/39 |
| 2008/0161874 | A1 | 7/2008 | Bennett et al. |
| 2010/0076255 | A1 | 3/2010 | Robertson et al. |
| 2011/0071590 | A1 | 3/2011 | Mounaim et al. |
| 2011/0301663 | A1 | 12/2011 | Wang et al. |
| 2012/0197339 | A1* | 8/2012 | Takagi ............... A61N 1/36007 607/41 |
| 2013/0253622 | A1* | 9/2013 | Hooven ................ A61B 18/14 607/101 |
| 2016/0023005 | A1* | 1/2016 | Perryman .......... A61N 1/37229 607/60 |
| 2016/0235978 | A1 | 8/2016 | Haessler et al. |
| 2016/0339239 | A1* | 11/2016 | Yoo ..................... A61N 1/0456 |
| 2017/0165497 | A1* | 6/2017 | Lu ....................... A61N 1/36017 |
| 2017/0239470 | A1* | 8/2017 | Wei ..................... A61N 1/0514 |
| 2018/0008185 | A1* | 1/2018 | Ramu ................... A61B 5/204 |
| 2018/0214691 | A1 | 8/2018 | Kristoffer et al. |
| 2021/0346695 | A1 | 11/2021 | Grill et al. |
| 2023/0059066 | A1 | 2/2023 | Sridhar |
| 2023/0121038 | A1 | 4/2023 | John et al. |

OTHER PUBLICATIONS

Abrams et al., The standardisation of terminology of lower urinary tract function: report from the Standardisation Sub-committee of the International Continence Society. Neurourol Urodyn. 2002;21(2):167-78.

Aldamanhori et al., Underactive bladder: Pathophysiology and clinical significance. Asian J Urol. Jan. 2018;5(1):17-21.

Andersson. Bladder underactivity. Eur Urol. Feb. 2014;65(2):399-401.

Barrington. The Component Reflexes of Micturition In the Cat. Part III. Brain. 1941;64(4):239-43.

Barrington. The Component Reflexes of Micturition in the Cat: Parts I and II. Brain. 1931;54(2):177-88.

Blaivas et al., Pubovaginal fascial sling for the treatment of complicated stress urinary incontinence. J Urol. Jun. 1991;145(6):1214-8.

Chai et al., New therapeutic directions to treat underactive bladder. Investig Clin Urol. Dec. 2017;58(Suppl 2):S99-S106.

Chen et al., Bilateral pudendal afferent stimulation improves bladder emptying in rats with urinary retention. BJU Int. Apr. 2012; 109(7):1051-8.

Christianson et al., Convergence of bladder and colon sensory innervation occurs at the primary afferent level. Pain. Apr. 2007;128(3):235-243.

Chuang et al., Intravesical protamine sulfate and potassium chloride as a model for bladder hyperactivity. Urology. Mar. 2003;61(3):664-70.

Di Benedetto. Clean intermittent self-catheterization in neurourology. Eur J Phys Rehabil Med. Dec. 2011;47(4):651-9.

Dieter et al., Characterizing the Bladder's Response to Onabotulinum Toxin Type A Using a Rat Model. Female Pelvic Med Reconstr Surg. Nov./Dec. 2016;22(6):467-471.

Dieter et al., The effects of bilateral bipolar sacral neurostimulation on urinary bladder activity during filling before and after irritation in a rat model. Neurourol Urodyn. Apr. 2015;34(4):387-91.

Drake et al., Voiding dysfunction due to detrusor underactivity: an overview. Nat Rev Urol. Aug. 2014;11(8):454-64.

Fraser et al., Best practices for cystometric evaluation of lower urinary tract function in muriform rodents. Neurourol Urodyn. Aug. 2020;39(6):1868-1884.

Fraser. New Insights into the Pathophysiology of Detrusor-Sphincter Dyssynergia. Current Bladder Dysfunction Reports. 2011;6(2):93-9.

Fukuda. [Effects of the pelvic and hypogastric nerve transection on the micturition cycle in the decerebrate dogs]. Hinyokika kiyo Acta urologica Japonica. 1987;33(10):1608-1617.

Garry et al., Reflexes involving the external urethral sphincter in the cat. J Physiol. Dec. 1959;149(3):653-65.

Goins et al., Herpes simplex virus mediated nerve growth factor expression in bladder and afferent neurons: potential treatment for diabetic bladder dysfunction. J Urol. May 2001;165(5):1748-54.

Gustafson et al., A urethral afferent mediated excitatory bladder reflex exists in humans. Neurosci Lett. Apr. 22, 2004;360(1-2):9-12.

Hoag et al., Underactive Bladder: Clinical Features, Urodynamic Parameters, and Treatment. Int Neurourol J. Sep. 2015;19(3):185-9.

Jung et al., Urethral afferent nerve activity affects the micturition reflex; implication for the relationship between stress incontinence and detrusor instability. J Urol. Jul. 1999;162(1):204-12.

Kakizaki et al., Reflex pathways controlling urethral striated and smooth muscle function in the male rat. Am J Physiol. May 1997;272(5 Pt 2):R1647-56.

Kakizaki et al., Reorganization of somato-urethral reflexes following spinal cord injury in the rat. J Urol. Oct. 1997;158(4):1562-7.

(56) References Cited

OTHER PUBLICATIONS

Kessler et al., Sacral neuromodulation for urinary retention. Nat Clin Pract Urol. Dec. 2008;5(12):657-66.
Kinoshita et al., Synthesis and evaluation of a potent, well-balanced EP 2/EP 3 dual agonist. Bioorg Med Chem. Jan. 1, 2018;26(1):200-214.
Klee et al., Detrusor contractility to parasympathetic mediators is differentially altered in the compensated and decompensated states of diabetic bladder dysfunction. Am J Physiol Renal Physiol. Aug. 1, 2019;317(2):F388-F398.
Kovacevic et al., Reflex neuromodulation of bladder function elicited by posterior tibial nerve stimulation in anesthetized rats. Am J Physiol Renal Physiol. Feb. 15, 2015;308(4):F320-9.
Lavrov et al., Facilitation of stepping with epidural stimulation in spinal rats: role of sensory input. J Neurosci. Jul. 30, 2008;28(31):7774-80.
Maggi et al., Analysis of factors involved in determining urinary bladder voiding cycle in urethan-anesthetized rats. Am J Physiol. Aug. 1986;251(2 Pt 2):R250-7.
McKenna et al., The organization of the pudendal nerve in the male and female rat. J Comp Neurol. Jun. 22, 1986;248(4):532-49.
Miyazato et al., The other bladder syndrome: underactive bladder. Rev Urol. 2013;15(1):11-22.
Nathan et al., Micturition reflexes in man. J Neurol Neurosurg Psychiatry. Aug. 1952;15(3):148-9.
Nishizawa et al., Role of the pelvic nerve in the dynamics of micturition in the decerebrate dog as determined by suprapubic endoscopical and urodynamic evaluation. J Urol. Aug. 1987;138(2):442-5.
Osman et al., Detrusor underactivity and the underactive bladder: a new clinical entity? A review of current terminology, definitions, epidemiology, aetiology, and diagnosis. Eur Urol. Feb. 2014;65(2):389-98.
Palacios et al., Neuroanatomic and behavioral correlates of urinary dysfunction induced by vaginal distension in rats. Am J Physiol Renal Physiol. May 1, 2016;310(10):F1065-73.
Persson et al., Morphological and functional evidence against a sensory and sympathetic origin of nitric oxide synthase-containing nerves in the rat lower urinary tract. Neuroscience. Mar. 1997;77(1):271-81.
Potts et al., Timing of sacral neurostimulation is important for increasing bladder capacity in the anesthetized rat. Am J Physiol Renal Physiol. Nov. 1, 2019;317(5):F1183-F1188.
Sasaki et al., Diabetic cystopathy correlates with a long-term decrease in nerve growth factor levels in the bladder and lumbosacral dorsal root Ganglia. J Urol. Sep. 2002;168(3):1259-64.
Sexton et al., The overlap of storage, voiding and postmicturition symptoms and implications for treatment seeking in the USA, UK and Sweden: EpiLUTS. BJU Int. Apr. 2009;103 Suppl 3:12-23.
Su et al., Neuromodulation in a rat model of the bladder micturition reflex. Am J Physiol Renal Physiol. Feb. 15, 2012;302(4):F477-86.
Torimoto et al., Urethral dysfunction in diabetic rats. J Urol. May 2004;171(5):1959-64.
Tyagi et al., Pathophysiology and animal modeling of underactive bladder. Int Urol Nephrol. Sep. 2014;46 Suppl 1(0 1):S11-21.
Tzeng et al., The Ethanol Extract of Zingiber zerumbet Attenuates Streptozotocin-Induced Diabetic Nephropathy in Rats. Evid Based Complement Alternat Med. 2013;2013:340645. 8 pages.
Xiao et al., Roles of polyuria and hyperglycemia in bladder dysfunction in diabetes. J Urol. Mar. 2013;189(3):1130-6.
Yamada et al., Efficacy of neuroselective and site-specific nociceptive stimuli of rat bladder. Urology. Feb. 2012;79(2):483.e7-12.
Yang et al., Diabetic urethropathy compounds the effects of diabetic cystopathy. J Urol. Nov. 2007;178(5):2213-9.
Yang et al., Differential vulnerabilities of urethral afferents in diabetes and discovery of a novel urethra-to-urethra reflex. Am J Physiol Renal Physiol. Jan. 2010;298(1):F118-24.
Yang et al., Voltage-dependent potassium currents of urethral afferent neurons in diabetes mellitus. Brain Res. Jun. 27, 2008;1217:132-8.
Yoo et al., Pudendal nerve stimulation evokes reflex bladder contractions in persons with chronic spinal cord injury. Neurourol Urodyn. 2007;26(7):1020-3.
Chew et al., "Pelvic autonomic nerve preservation in radical rectal cancer surgery: changes in the past 3 decades," Gastroenterology Report, 2016, 4(3): 173-185.
Karam et al., "Innervation of the Female Human Urethral Sphincter: 3D Reconstruction of Immunohistochemical Studies in the Fetus" European Urology, 2005, 47 (2005) 627-634.
Karam et al., "The Precise Location and Nature of the Nerves to the Male Human Urethra: Histological and Immunohistochemical Studies with Three-Dimensional Reconstruction" European Urology, 2005, 48: 858-864.
Raz, The Anatomy of Pelvic Support. In: Atlas of Vaginal Reconstructive Surgery, $1^{st}$ ed., Springer, New York, NY. [online]. 2015 [retrieved on Feb. 17, 2025]. Retrieved from the internet: < URL: https://doctorlib.org/surgery/atlas-vaginal-reconstructive-surgery/1.html>.
Rojas-Gómez et al., "Regional anesthesia guided by ultrasound in the pudendal nerve territory" Colombian Journal of Anesthesiology, Jul.-Sep. 2017, 45(3): 200-209.

\* cited by examiner

DEVICES, SYSTEMS, AND METHODS FOR PROMOTING VOIDING IN SUBJECTS WITH UNDERACTIVE BLADDERS

RELATED APPLICATIONS

This application claims priority to and the benefit of U.S. Provisional Patent Application No. 62/880,239 filed Jul. 30, 2019, which is incorporated herein by reference in its entirety for all purposes.

FIELD

This present disclosure provides devices, systems, and methods for the treatment of conditions pertaining to bladder control. In particular, the present disclosure provides devices, systems, and methods directed to the application of electrical stimulation to the proximal urethra and associated nervous tissue to elicit voiding contractions that normalize bladder function.

BACKGROUND

The International Continence Society broadly characterizes underactive bladder (UAB) by a "slow urinary stream, hesitancy and straining to void, with or without a feeling of incomplete bladder emptying sometimes with storage symptoms." Detrusor Underactivity (DU), however, is a more specific pressure-flow urodynamic diagnosis with multiple formulaic definitions. DU is associated with bladder emptying symptoms, upper urinary tract deterioration, and recurrent urinary tract infections. Neurogenic etiologies include spinal trauma and congenital disease, stroke, peripheral nerve trauma secondary to pelvic surgeries and trauma, diabetes mellitus, and neurological disorders. Myogenic etiologies include diabetes mellitus and long-term bladder outlet obstruction. DU was observed in 99-28% of men <50 years of age and in 48% of men >70 years of age with "non-neurogenic" lower urinary tract symptoms, suggesting a role for aging. Overall, it is very difficult to ascertain true prevalence of DU because only those with symptoms significant enough to justify invasive urodynamic testing receive a diagnosis.

DU has few available treatment options. Medically, drug options included alpha-blockers, 5-alpha reductase inhibitors, and poorly efficacious, non-specific parasympathomimetics. Catheterization has become a mainstay of the management of DU patients of various etiologies; however, infections, urethral trauma, and bladder stones are not uncommon consequences. Sacral neuromodulation, utilized for overactive bladder, also appears to be somewhat efficacious for non-obstructive urinary retention, but the mechanisms for these effects are poorly understood.

SUMMARY

Embodiments of the present disclosure include a system that comprises an electrical pulse generator configured to deliver a plurality of pulses based on input associated with inducement of at least one physiological response, and a plurality of electrodes functionally coupled to the pulse generator and configured for placement on proximal urethra tissue (including and any associated nerves (e.g., nerves within and immediately adjacent to the urethral tissue)) of a subject. In accordance with these embodiments, the pulse generator includes a power source, and activation of the pulse generator causes the plurality of pulses to be delivered from the plurality of electrodes, thereby inducing the at least one physiological response in the subject.

In some embodiments, the plurality of pulses are delivered at a frequency from about 1 Hz to about 100 Hz. In some embodiments, the plurality of pulses are delivered at a frequency from about 10 Hz to about 75 Hz. In some embodiments, the plurality of pulses are delivered at a frequency from about 20 Hz to about 50 Hz.

In some embodiments, the plurality of pulses are delivered at about 1 V to about 75 V. In some embodiments, the plurality of pulses are delivered at about 10 V to about 50 V.

In some embodiments, plurality of pulses are delivered at durations from about 0.01 to about 1.0 ms. In some embodiments, the plurality of pulses are delivered at durations of about 0.1 ms.

In some embodiments, the plurality of pulses are delivered at a 30 s on/60 s off pattern. In some embodiments, the plurality of pulses are delivered at a 60 s on/120 s off pattern.

In some embodiments, the at least one physiological response comprises at least one of bladder voidance contractions, voiding-associated rhabdosphincter relaxation, and urethral circumferential smooth muscle relaxation.

In some embodiments, the plurality of electrodes comprises any electrodes ranging from monopolar electrodes to dipolar electrodes. In some embodiments, the plurality of electrodes are placed orthogonally across the proximal urethra and immediate margins and spaced about 0.1 cm to about 2.0 cm apart. In some embodiments, the plurality of electrodes comprises a flexible electrode support comprising integrated bipolar electrodes. In some embodiments, the thin flexible electrode support comprising integrated bipolar electrodes is placed in the mid-to-proximal urethra area.

In some embodiments, the at least one physiological response is induced in the subject in the absence of a somatomotor response.

In some embodiments, the pulse generator is external to the subject, and wherein the pulse generator is wirelessly coupled to the plurality of electrodes. In some embodiments, the pulse generator is internal to the subject, and wherein the pulse generator is directly coupled to the plurality of electrodes.

In some embodiments, the system further includes an external controller functionally coupled to the pulse generator; the controller provides input to the pulse generator to induce the at least one physiological response.

In some embodiments, the pulse generator comprises a programmable microprocessor.

In some embodiments, the power source comprises a battery external to the subject. In some embodiments, the power source comprises a battery internal to the subject.

Embodiments of the present disclosure also include a method for delivering a plurality of electrical pulses to proximal urethra and any associated nerves (e.g., nerves within and immediately adjacent to the urethral tissue) of a subject using any of the embodiments of the system described above. In accordance with these embodiments, the method includes manipulating a controller to provide input to the pulse generator, and activating the pulse generator to cause a plurality of pulses to be delivered to a plurality of electrodes to induce at least one physiological response.

In some embodiments, the at least one physiological response comprises bladder voidance contractions.

In some embodiments, manipulating the controller comprises selecting pre-determined input parameters associated with the at least one physiological response. In some embodiments, the pre-determined input parameters comprise one or more of pulse frequency, voltage, duration, amplitude and/or pattern.

In some embodiments, the method improves at least one symptom associated with underactive bladder in the subject Embodiments of the present disclosure also include use of any of the embodiments of the system described above in a method for delivering a plurality of electrical pulses to proximal urethra and any associated nerves (e.g., nerves within and immediately adjacent to the urethral tissue) of a subject. In accordance with these embodiments, the method includes manipulating a controller to provide input to the pulse generator, and activating the pulse generator to cause a plurality of pulses to be delivered to a plurality of electrodes to induce at least one physiological response.

Embodiments of the present disclosure also include a method of treating underactive bladder in a subject. In accordance with these embodiments, the method includes manipulating a controller to provide input associated with inducement of at least one physiological response to a pulse generator, the pulse generator configured to generate a plurality of pulses based on the input, and activating the pulse generator to cause the plurality of pulses to be delivered from a plurality of electrodes. The plurality of electrodes are functionally coupled to the pulse generator and in contact with proximal urethra and any associated nerves (e.g., nerves within and immediately adjacent to the urethral tissue) in the subject such that activation of the pulse generator induces the at least one physiological response in the subject.

In some embodiments, the subject has been diagnosed with Detrusor Underactivity (DU).

In some embodiments, the at least one physiological response comprises at least one of bladder voidance contractions, voiding-associated rhabdosphincter relaxation, and urethral circumferential smooth muscle relaxation.

In some embodiments, manipulating the controller comprises selecting re-determined input parameters associated with the at least one physiological response.

In some embodiments, the pre-determined input parameters comprise one or more of pulse frequency, voltage, duration, amplitude and/or pattern.

In some embodiments, the method improves at least one symptom of underactive bladder in the subject.

In some embodiments, the method further comprises administering a therapeutic agent to the subject before, during, or after the activation of the pulse generator.

In some embodiments, the therapeutic agent comprises one or more of a nonspecific or M3 specific muscarinic agonist, a parasympathomimetic, an M3 muscarinic receptor positive allosteric modulator, a sensory afferent transmission enhancing compound, a GABA receptor antagonist, and/or a Glycine receptor antagonist, and any combinations thereof.

Embodiments of the present disclosure also include use of an electrical stimulation system in a method for treating underactive bladder in a subject. In accordance with these embodiments, the method includes manipulating a controller to provide input associated with inducement of at least one physiological response to a pulse generator, the pulse generator configured to generate a plurality of pulses based on the input, and activating the pulse generator to cause the plurality of pulses to be delivered from a plurality of electrodes. The plurality of electrodes are functionally coupled to the pulse generator and in contact with proximal urethra and any associated nerves (e.g., nerves within and immediately adjacent to the urethral tissue) in the subject such that activation of the pulse generator induces the at least one physiological response in the subject.

BRIEF DESCRIPTION OF THE DRAWINGS

FIG. 1A includes a representative schematic of a system for the application of electrical stimulation to the proximal urethra to elicit voiding contractions in a subject. FIG. 1B includes representative images corresponding to the testing of the system in adult female Sprague-Dawley rats (Phase one preparation via laparotomy). Note cystometric transvesical catheter, bilateral ureteral diversion catheters, and exposed urethra after symphysectomy with electrode placement (left panel). Asymmetric (left-side only) voiding contraction after right pelvic nerve transection (PNx), phase two preparation (right panel). Note that preparation utilizes a thin flexible electrode support with integrated bipolar electrodes.

DETAILED DESCRIPTION

Figure 1A:
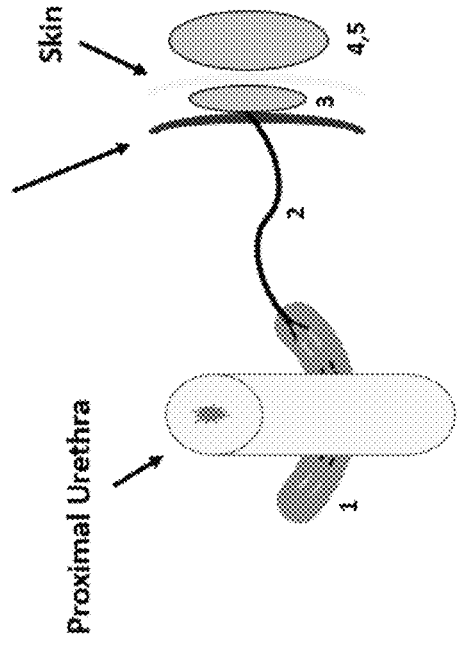
FIGS. 1A-1B.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

"Therapy" and/or "therapy regimen" generally refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. In some embodiments, the treatment comprises electrical stimulation to the proximal urethra to elicit voiding contractions that normalize bladder function.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, neurobiology, microbiology, genetics, electrical stimulation, neural stimulation, neural modulation, and neural prosthesis described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. DEVICES AND SYSTEMS FOR URETHRAL ELECTROSTIMULATION

This present disclosure provides devices, systems, and methods for the treatment of conditions pertaining to bladder control. In particular, the present disclosure provides devices, systems, and methods directed to the application of electrical stimulation to the proximal urethra and associated nervous tissue to elicit voiding contractions that normalize bladder function.

As context for the inventive subject matter described herein, Barrington's discoveries of urethra-to-bladder reflexes in cats from the early 1900s provide a potential therapeutic target for treating certain bladder conditions. Barrington's Reflexes (BR) 2, 3, and 7 resulted in excitatory detrusor activity via afferents from the proximal urethra. BR2 is a pudendal nerve reflex stimulating a voiding contraction, BR3 is a hypogastric reflex stimulating a non-voiding contraction, and BR7 is a pelvic nerve reflex stimulating a voiding contraction. Another reflex, BR4 results in relaxation of the rhabdosphincter via pudendal afferents in response to intraluminal flow, which also promoted voiding. Flow-dependent urethra-to-bladder reflexes have also been described. Collectively, these reflexes represent a positive feedback mechanism for efficient voiding.

Based on Barrington's reflexes, extraluminal proximal urethral electrical stimulation (PUES) was developed to induce bladder contractions. Electrodes were placed in the mid-to-proximal pelvic urethra area, where the pelvic and hypogastric afferents course proximal-to-distal from the major pelvic ganglia and the pudendal afferents course distal-to-proximal from the sacral plexus. By field stimulating the urethral serosal surface and immediately adjacent tissue, afferent fibers from all nerves both intramurally and extramurally were included. A two-phase exploratory rat study was conducted to apply stimulation under conditions of neurogenic UAB. In phase one, electrical field stimulation (EFS) was applied with bipolar electrodes positioned over the exposed ventral proximal urethra in normal rats. In phase two, experiments were conducted to investigate whether a thin flexible electrode support with integrated bipolar electrodes, placed dorsally in an anatomically-similar position to that of a urethral sling, could improve bladder function in the setting of underactive bladder (UAB) caused by unilateral pelvic nerve transection (PNx).

In accordance with the above, electrical field stimulation of the proximal urethras of urethane-anesthetized rats was performed in order to produce bladder contractions in the settings of neurologically-intact, and unilateral pelvic nerve transected rats (latter two conditions as proxies for underactive bladder). Results described further herein demonstrate that proximal urethral electrical stimulation elicits voiding contractions that normalize bladder function in setting of a validated unilateral pelvic nerve transection model for underactive bladder in rats. In particular, in spinal-intact rats, PUES at 20 Hz and 30-40V elicited reliable bladder contractions, often in the absence of somatomotor responses; thin flexible electrode support-mounted electrodes between urethra and vagina prevented somatomotor response in subsequent experiments. The validated unilateral PNx model induces conditions of increased TBC and decreased VE which effectively proxy for underactive bladder. Following PNx, PUES with posterior stimulation at 20-30 Hz (50V) reliably elicited voiding contractions with normal VE at greatly reduced (normal) fill volumes without somatomotor activation, thereby normalizing functional voiding in this underactive bladder model.

Phase one results demonstrated reliable and consistent bladder contractions from PUES in spinal-intact rats within a specific range of stimulus parameters. The PUES approach does not discriminate among which nerve's afferents (pelvic, hypogastric or pudendal) contributed to the reflex. Regardless, the results following SCI demonstrate that the observed PUES-evoked contractions are not due to direct detrusor stimulation because the bladders did not respond to PUES after SCI but did still contract with direct contact. Additionally, BRs appear to require some suprasacral spinal involvement. The latter finding is interesting as sacral bladder-to-urethra external urethral sphincter guarding and smooth muscle relaxant reflexes remain intact under the same conditions (unpublished observations).

Pelvic surgery is a known etiology for UAB presumed to involve at least unilateral pelvic nerve injury. A significant increase in TBC and a decrease in VE was found after unilateral PNx that was not demonstrated in sham-PNx rats, thereby eliminating the possibility that results were due to the cystometric testing procedure over time and validating the model. Both unilateral and bilateral pelvic nerve transection have previously been described as models for underactive bladder; however, the results provided herein are the first fully validated acute model with appropriate in series and parallel controls.

Although yet to be validated in a human subject, other studies have demonstrated that in chronic spinal cord injured men with sufficient bladder volumes, electrical stimulation of the proximal urethral can stimulate detrusor contraction. Such results may, however, represent a mass reflex, rather than a voiding reflex one would expect from BR. Interestingly, successful surgical repair of SUI in mixed urge-stress incontinent women results in a cure of the urge component in 50-75% of patients. This finding suggests that urine in the proximal urethra may trigger a voiding contraction in humans, and therefore, represents evidence of an excitatory BR in humans and the likely applicability of PUES. As more experiments are performed to determine the exact mechanism and utility of PUES in animal models, investigations have also started to define an initial subset of human subjects who may benefit from PUES; first index patients would be otherwise neurologically intact women with DU clearly time-associated with pelvic surgery. Obviously, patients who would not achieve benefit would be those with complete bilateral losses of urethral afferents and bladder efferent nerve connectivity.

As described further herein, embodiments of the present disclosure include a system (e.g., to carry out the PUES approach described herein) that comprises an electrical pulse generator configured to deliver a plurality of electrical pulses based on input associated with inducement of at least one physiological response, and a plurality of electrodes functionally coupled to the pulse generator and configured for placement on proximal urethra tissue of a subject sufficient to stimulate associated nerves (e.g., autonomic and pudendal sensory nerves). In accordance with these embodiments, the pulse generator generally includes a power source, and activation of the pulse generator causes the plurality of pulses to be delivered from the plurality of electrodes, thereby inducing the at least one physiological response in the subject.

For example, FIG. 1A includes a representative schematic of systems and devices of the present disclosure for applying electrical stimulation to the proximal urethra to elicit voiding contractions in a subject. As shown, the system includes a plurality of electrodes (1), or stimulating electrodes (e.g., bipolar electrodes), that are placed on the proximal tissue of the urethra of a subject, including any associated nervous tissue. In some embodiments, the plurality of electrodes (1) are coupled directly to lead wires (2) that extend to a pulse generator or stimulation unit (3). In some embodiments, the pulse generator (3) is implantable in the subject (FIG. 1A). For example, the pulse generator can be a magnetically-triggered implantable stimulation unit that includes a rechargeable battery, although other configurations of pulse generators can also be used, as would be recognized by one of skill in the art based on the present disclosure. In some embodiments, the pulse generator is external to the subject, and the pulse generator is wirelessly coupled to the plurality of electrodes. In some embodiments, the pulse generator is internal to the subject, and the pulse generator is directly coupled to the plurality of electrodes.

In some embodiments, the plurality of electrodes comprises any electrodes ranging from monopolar electrodes to dipolar electrodes. In some embodiments, the plurality of electrodes are placed orthogonally across the proximal urethra and immediate margins and spaced about 0.1 cm to about 2.0 cm apart. In some embodiments, the plurality of electrodes are spaced about 0.1 cm to about 1.5 cm apart. In some embodiments, the plurality of electrodes are spaced about 0.1 cm to about 1.0 cm apart. In some embodiments, the plurality of electrodes are spaced about 0.5 cm to about 2.0 cm apart. In some embodiments, the plurality of electrodes are spaced about 0.5 cm to about 1.5 cm apart. In some embodiments, the plurality of electrodes are spaced about 0.5 cm to about 1.0 cm apart. In some embodiments, the plurality of electrodes comprises a flexible electrode support comprising integrated bipolar electrodes. In some embodiments, the flexible electrode support comprising integrated bipolar electrodes is placed in the mid-to-proximal urethra area.

In some embodiments, the system can include an external magnetic or radio unit (4) that can be configured to activate/deactivate the pulse generator (3). This external controller can be used to send activation/deactivation signals (e.g., on-demand) to the pulse generator (3) to induce the generation of a plurality of electrical pulses from the electrodes (1), which stimulate bladder voidance contractions in the subject for a certain period of time sufficient to induce bladder voidance. Additionally, the systems and devices of the present disclosure can also include a power source, such as an external charging unit (5), for providing power to the pulse generator.

In some embodiments, the pulse generator can include a power source comprising a battery and a programmable microprocessor coupled to the battery, and the pulse generator can be generally configured to generate electrical signals for delivering a plurality of electrical pulses having certain characteristics or a certain pattern of electrical stimulation capable of inducing a physiological response in a subject. In some embodiments, the system further includes a controller comprising hardware, software, firmware, or combinations thereof for implementing functionality described herein. For example, the controller can be implemented by one or more microprocessors and memory. The controller can be operatively connected to the pulse generator to facilitate the generation of electrical signals and applying temporal patterns of electrical stimulation to targeted urethral tissue. The output signals may be received by the connection lead and carried to the electrode or electrodes for the delivery of electrical stimulation to targeted urethral tissue. In some embodiments, such as when both the pulse generator and power source are implanted in a subject, activation of the pulse generator can include activation using a smartphone (e.g., smartphone application as the controller). In some cases, activation of the pulse generator using a smartphone can serve as a backup in the event a main controller is inoperable or out of range.

As would be recognized by one of ordinary skill in the art based on the present disclosure, the systems and devices described herein are used to deliver a plurality of electrical pulses to a subject in an effort to induce a desired physiological response in the subject (e.g., induce bladder avoidance contractions to treat underactive bladder conditions). In accordance with these embodiments, the systems and devices of the present disclosure can be used to deliver a variety of electrical stimulations based on pre-determined input parameters that include, but are not limited to, pulse frequency, voltage, duration, amplitude and/or pattern. These input parameters can be adjusted based on a variety of clinical factors to treat a patient, such as but not limited to, the condition being treated, patient characteristics, biomarker information, and/or information from a clinical diagnosis.

In some embodiments, the physiological response is induced to treat one or more symptoms associated with a bladder condition, such as underactive bladder. In some embodiments, the physiological response includes, but is not limited to, bladder voidance contractions, voiding-associated rhabdosphincter relaxation, and urethral circumferential smooth muscle relaxation. Other physiological responses currently known or subsequently discovered to be associated with a bladder disease or condition can also be induced using the systems and methods of the present disclosure. As described further herein, the physiological response can be induced in the subject in the absence of an undesired physiological response in the subject. For example, the systems and devices of the present disclosure can be used to induce bladder voidance contractions without concomitant activation of a somatomotor response.

In some embodiments, the plurality of pulses are delivered at a frequency from about 1 Hz to about 100 Hz. In some embodiments, the plurality of pulses are delivered at a frequency from about 10 Hz to about 75 Hz. In some embodiments, the plurality of pulses are delivered at a frequency from about 20 Hz to about 50 Hz. In some embodiments, the plurality of pulses are delivered at a frequency from about 10 Hz to about 60 Hz. In some embodiments, the plurality of pulses are delivered at a frequency from about 10 Hz to about 50 Hz. In some embodiments, the plurality of pulses are delivered at a frequency from about 10 Hz to about 40 Hz. In some embodiments, the plurality of pulses are delivered at a frequency from about 10 Hz to about 30 Hz.

In some embodiments, the plurality of pulses are delivered at about 1 V to about 75 V. In some embodiments, the plurality of pulses are delivered at about 10 V to about 50 V. In some embodiments, the plurality of pulses are delivered at about 10 V to about 40 V. In some embodiments, the plurality of pulses are delivered at about 10 V to about 30 V. In some embodiments, the plurality of pulses are delivered at about 10 V to about 20 V. In some embodiments, the plurality of pulses are delivered at about 20 V to about 100 V. In some embodiments, the plurality of pulses are delivered at about 20 V to about 90 V. In some embodiments, the plurality of pulses are delivered at about 20 V to about 80 V. In some embodiments, the plurality of pulses are delivered at about 20 V to about 70 V. In some embodiments, the plurality of pulses are delivered at about 20 V to about 60 V. In some embodiments, the plurality of pulses are delivered at about 30 V to about 60 V. In some embodiments, the plurality of pulses are delivered at about 40 V to about 60 V.

In some embodiments, plurality of pulses are delivered at durations from about 0.01 to about 1.0 ms. In some embodiments, plurality of pulses are delivered at durations from about 0.05 to about 1.0 ms. In some embodiments, plurality of pulses are delivered at durations from about 0.1 to about 1.0 ms. In some embodiments, plurality of pulses are delivered at durations from about 0.1 to about 0.5 ms. In some embodiments, the plurality of pulses are delivered at durations of about 0.1 ms, 0.2 ms, 0.3 ms, 0.4 ms, or 0.5 ms.

In some embodiments, the plurality of pulses are delivered at a 30 s on/30 s off pattern. In some embodiments, the plurality of pulses are delivered at a 30 s on/60 s off pattern. In some embodiments, the plurality of pulses are delivered at a 30 s on/90 s off pattern. In some embodiments, the plurality of pulses are delivered at a 30 s on/120 s off pattern. In some embodiments, the plurality of pulses are delivered at a 60 s on/30 s off pattern. In some embodiments, the plurality of pulses are delivered at a 60 s on/60 s off pattern. In some embodiments, the plurality of pulses are delivered at a 60 s on/90 s off pattern. In some embodiments, the plurality of pulses are delivered at a 60 s on/120 s off pattern. In some embodiments, the plurality of pulses are delivered at a 30 s off/90 s on pattern. In some embodiments, the plurality of pulses are delivered at a 30 s off/120 s on pattern. In some embodiments, the plurality of pulses are delivered at a 60 s off/90 s on pattern. In some embodiments, the plurality of pulses are delivered at a 60 s off/120 s on pattern.

In some embodiments, the plurality of electrical pulses can have a waveform(s) that is optimized for a given function. Waveform(s) that can be generated using the systems and devices of the present disclosure can have any suitable shape, including but not limited to square waves, rectangular waves, triangular waves, and saw-toothed waves. Waveform(s) of the present disclosure can also be uni-directional, bi-directional, periodic, non-periodic, symmetrical, non-symmetrical, simple, or complex. In some embodiments, the shape of the optimized waveform can be described as or based on a sum of sinusoidal functions, a sum of Gaussian functions, or a sum of any other functional forms, as would be recognized by one of ordinary skill in the art based on the present disclosure.

In some embodiments, the systems and devices of the present disclosure include an external computing device that is not implanted within a subject. The computing device can communicate with a device or system via any suitable communication link (e.g., a wired, wireless, or optical communication link). The communication link may also facilitate battery recharge. In one embodiment, a clinician or medical professional may interact with a user interface of the computing device for programming the output of the implanted pulse generator, for example, based on pre-determined input parameters associated with inducing a particular physiological response in a subject. In accordance with these embodiments, systems and methods of the present disclosure can be used to deliver a plurality of electrical pulses, as described herein, to treat a symptom of a bladder condition. In some embodiments, systems and methods of the present disclosure can be implemented as an algorithm within a pulse generator device. A controller can deliver multiple frequencies and patterns of electrical pulses through different output channels to different contacts on the stimulation electrode in contact with proximal urethra tissue and associated nervous tissue (e.g., autonomic and pudendal sensory nerves). Alternatively, the system can be pre-programmed with specific combinations of input parameters.

In some embodiments, computer readable program instructions for carrying out methods of the present disclosure, including programming the pulse generator to output the plurality of electrical pulses, can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the subject matter of the present disclosure.

3. METHODS OF TREATMENT

Embodiments of the present disclosure include a method for delivering a plurality of electrical pulses to proximal urethra tissue and associated nervous tissue of a subject using any of the embodiments of the systems and devices described herein. In accordance with these embodiments, the method includes manipulating a controller to provide input to the pulse generator. The input provided to the pulse generator can include any information or signals pertaining to the operation of the pulse generator, including but not limited to, activating/deactivating the pulse generator for certain periods of time (prescribed or on-demand), as well as adjusting one or more input parameters (e.g., pulse frequency, voltage, duration, amplitude and/or pattern) associated with the plurality of pulses generated by the electrodes. In this manner, the user (patient or medical professional) can manipulate the controller to cause the pulse generator to deliver a plurality of electrical pulses to tissue of the proximal urethra in order to induce a desired physiological response (e.g., stimulate bladder voidance contractions). Thus, in some embodiments, the method includes activating the pulse generator to cause a plurality of pulses to be delivered to a plurality of electrodes to induce at least one physiological response. In some embodiments, the physiological response that is induced includes, but is not limited to, a physiological response intended to treat or alleviate a symptom of a bladder condition. In some embodiments, the physiological response that is induced is at least one of bladder voidance contractions, voiding-associated rhabdosphincter relaxation, and urethral circumferential smooth muscle relaxation, although other responses can also be induced.

In some embodiments, manipulating the controller comprises selecting pre-determined input parameters associated with the at least one physiological response. In some embodiments, the pre-determined input parameters include, but are not limited to, one or more of pulse frequency, voltage, duration, amplitude and/or pattern. These input parameters can be adjusted by the user or medical professional based on a variety of factors in an effort to administer a treatment for a disease or condition associated, for example, with underactive bladder. The input parameters can be adjusted based on the specific symptom or condition being treated, individual patient characteristics, biomarker information, and/or information associated with a clinical assessment of the patient.

As described further herein, embodiments of the present disclosure include use of any of the embodiments of the devices/systems described herein in a method for delivering a plurality of electrical pulses to proximal urethra and associated nervous tissue of a subject to improve (e.g., treat, alleviate, etc.) at least one symptom associated with underactive bladder in the subject. In accordance with these embodiments, the method includes manipulating a controller to provide input associated with inducement of at least one physiological response to a pulse generator, the pulse generator configured to generate a plurality of pulses based on the input, and activating the pulse generator to cause the plurality of pulses to be delivered from a plurality of electrodes. The plurality of electrodes are functionally coupled to the pulse generator and in contact with proximal urethra tissue in the subject such that activation of the pulse generator induces the at least one physiological response in the subject.

In some embodiments, the subject has been diagnosed with Detrusor Underactivity (DU). DU is generally defined as a contraction of reduced strength and/or duration, resulting in prolonged bladder emptying and/or a failure to achieve complete bladder emptying within a normal time span. DU may influence the clinical presentation and impede the therapy of disorders as common and as disparate as detrusor overactivity, urinary retention, and benign prostatic hyperplasia. Urodynamically, nearly two-thirds of incontinent nursing home residents exhibit DU. The clinical diagnosis of DU when present alone or in association with other bladder conditions such as detrusor overactivity (detrusor hyperactivity with impaired contractility (DHIC)) is challenging, because symptoms lack adequate precision. DU has few available treatment options. Medically, these include non-specific drug options included alpha-blockers, 5-alpha reductase inhibitors, and poorly efficacious parasympathomimetics. Catheterization has become a mainstay of the management of DU patients of various etiologies; however, infections, urethral trauma, and bladder stones are not uncommon consequences. Thus, the systems, devices, and methods of the present disclosure provide a novel approach for treating subjects diagnosed with DU in a manner that is minimally invasive and significantly more effective than current treatment options.

Methods of the present disclosure also include assessing whether a subject diagnosed as having DU is a candidate for being treated with urethral electrostimulation designed to elicit a bladder voidance response, as described further herein, including the likelihood that such treatment will be effective. In some embodiments, assessing whether a subject is a candidate for urethral electrostimulation includes performing a diagnostic test. In some embodiments, the diagnostic test includes assessing the candidate subject using various clinical evaluations (e.g., voidance frequency, volume, efficiency, etc.). In some embodiments, the diagnostic test includes assessing the subject using biochemical approaches (e.g., biomarker data, genetic profiling, etc.).

Once sufficient diagnostic information is received regarding the suitability of the candidate subject for treatment with urethral electrostimulation, the methods provided herein can also include treating the subject with urethral electrostimulation in an effort to improve a symptom associated with a bladder condition, using the systems and devices of the present disclosure. In some embodiments, the method includes administering a therapeutic agent to the subject before, during, or after the pulse generator delivers electrostimulation to the subject. In some embodiments, the therapeutic agent comprises one or more of a nonspecific or M3 specific muscarinic agonist, a parasympathomimetic (e.g., bethanechol), an M3 muscarinic receptor positive allosteric modulator (e.g., ASP8302), a sensory afferent transmission enhancing compound (e.g., glutamate receptor agonists such as NMDA), a GABA receptor antagonist (e.g., bicucilline, securinine, metrazol, and flumazenil), and/or a Glycine receptor antagonist (e.g., brucine, tutin and caffeine), and any combinations thereof. The therapeutic agent can be administered in accordance with accepted methods (e.g., orally, intravenously, intramuscularly, intraperitoneally, etc.). In some embodiments, the therapeutic agent is administered peripherally or intrathecally in small quantities at the level of the sacral spinal cord.

4. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

For phase one, the proximal urethral ventral surface was stimulated using a bipolar electrode onlay (5-100 Hz, 10-50V) after pubic symphysectomy. The presence/absence of bladder contractions and lower extremity motor activity were recorded. For phase two, a novel approach was used, which included a thin flexible electrode support with integrated bipolar electrodes, placed in an anatomically similar position to a mid-urethral sling and stimulated following unilateral pelvic nerve transection. Total bladder capacities and voiding efficiencies were measured before and after pelvic nerve transection.

Figure 1B:
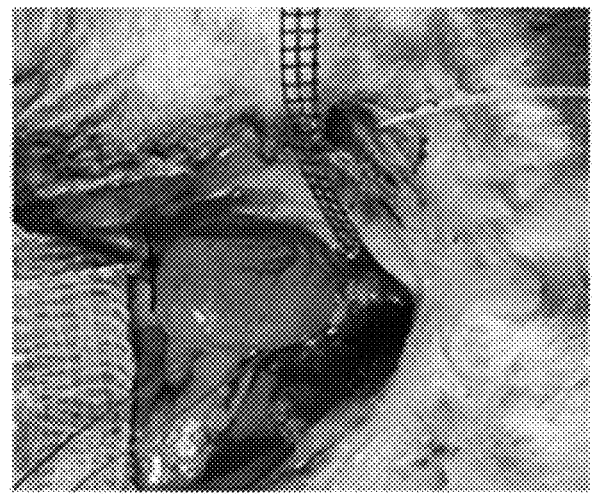
Figure 1B:
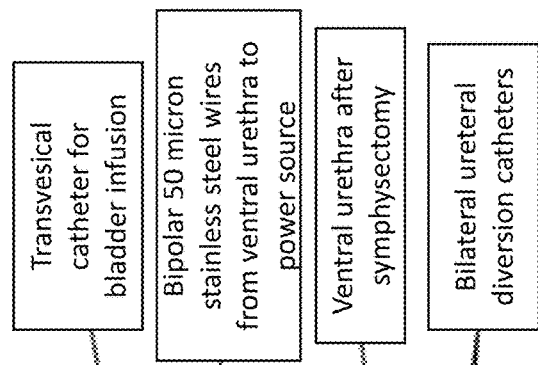
Figure 1B:
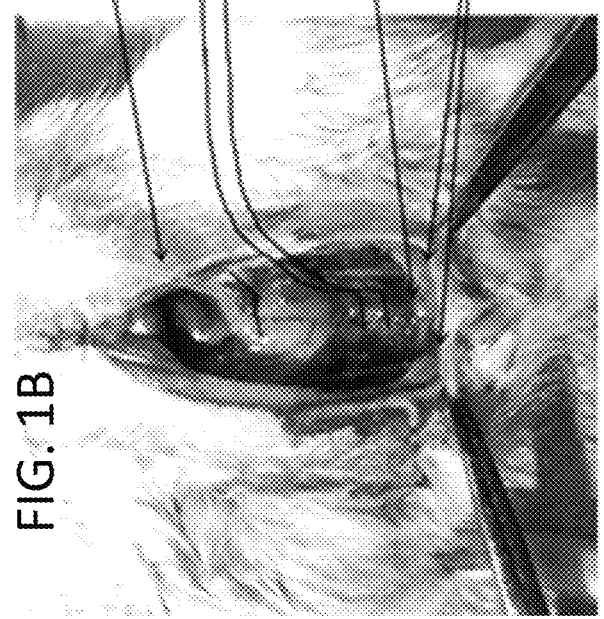

In phase one, seventeen urethane-anesthetized (1.5 g/kg sc) adult female Sprague-Dawley rats received a transvesical cystometry catheter (fire-flared tipped PE-50) and bilateral ureteral diversion catheters (PE-10). The pubis was removed to expose the proximal urethra (FIG. 1B, left). Following continuous cystometry at flow rate of 0.1 ml/min to ensure spontaneous reflex activity (≥20 min), the bladder infusion was stopped immediately following a voiding contraction. If no further contractions were observed within a 5 minute period, the bladder was deemed stable and PUES was applied using two ~0.6 cm long, 50 µm diameter Teflon-coated electrodes (M.T. Giken, Tokyo, Japan) placed orthogonally across the proximal urethra and immediate margins (~0.3 cm apart). PUES was applied for a 30 s on/60 s off pattern using 0.1 ms pulse durations, with frequencies and intensities systematically varied (5-100 Hz in 1/3 log steps and 10-50V in decade steps, respectively) using a Grass S88 Stimulator (Grass Technologies, West Warwick, R.I.). A broad range of frequencies based on test parameters found in the literature utilizing pudendal, tibial, and sacral neurostimulation were chosen.

Measurements included presence or absence of bladder contractions and/or lower extremity motor activity. Stimulation responses were assigned a score of +2 if bladder only response, +1 for bladder and somatomotor response, 0 for no observable response, and −1 for only somatomotor response. Data were analyzed graphically and stimulation frequencies with non-negative results across the voltage ranges were further analyzed using mixed-effects analysis with Sidak's MCT.

Figure 2:
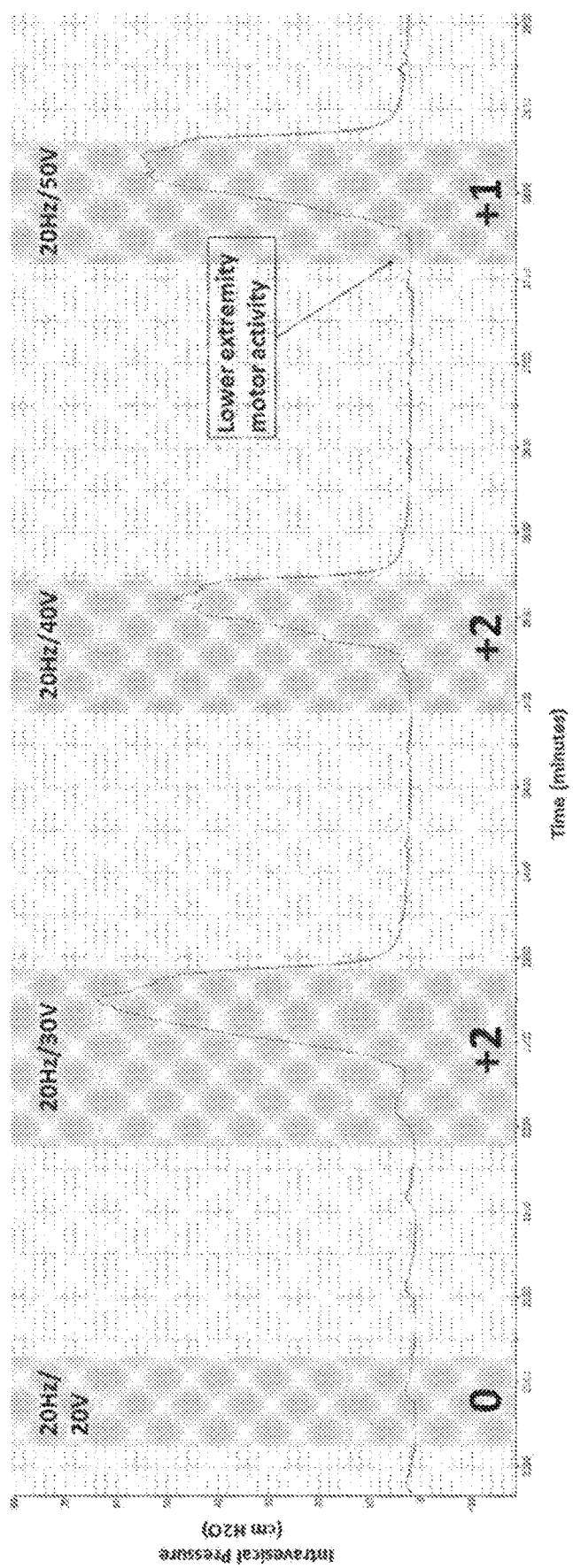
FIG. 2: Phase one cystometrogram with scoring. From right-to-left, 20 Hz with increasing voltage. Note no contraction at 20V (score of 0), contractions without lower extremity somatomotor activity at 30V and 40V (score of +2), and contraction with lower extremity somatomotor activity at 50V (score of +1).
Figure 3:
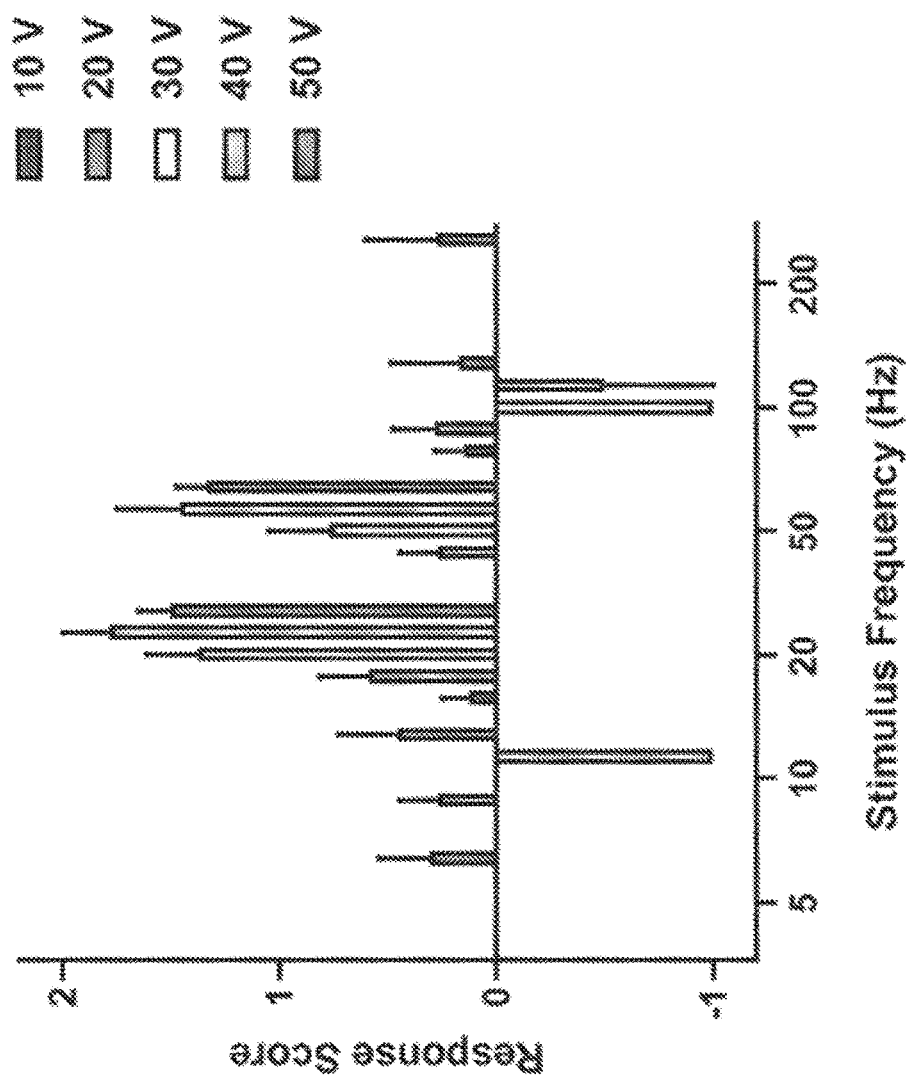
FIG. 3: Phase one frequency and voltage responses. Note overall positive scores for 20 Hz and 50 Hz across voltages (n=17 rats).
Figure 4:
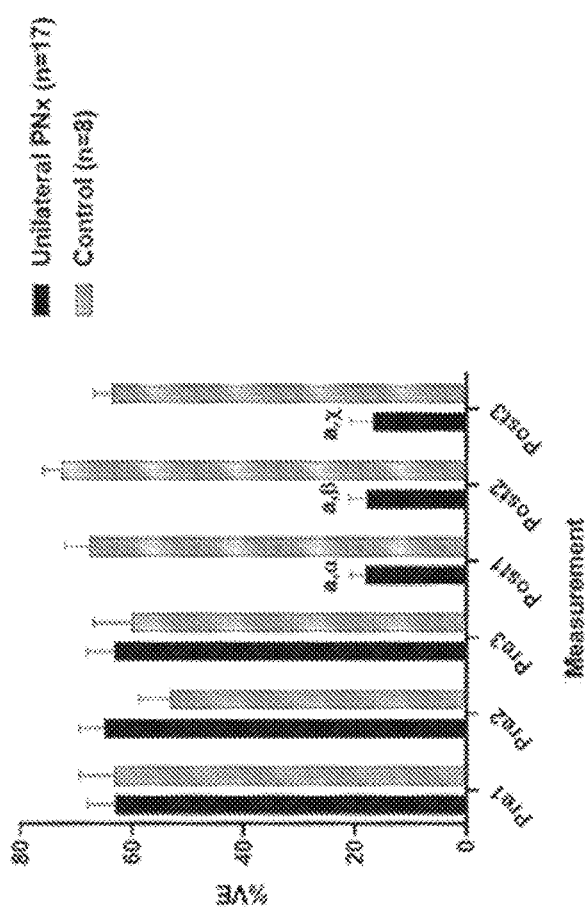
FIG. 4: Representative results validating unilateral pelvic nerve transection (PNx; black bars; n=17). Data demonstrates significant increases in true bladder capacity (TBC; left panel) and significant decreases in VE (right panel) when compared to control (sham PNx rats; gray bars; n=8). For TBC: $^{a}P<0.0001$ vs. Pre1-3 by Tukey's multiple comparison test (MCT), $^{\alpha}P=0.0027$, $^{\beta}P=0.0335$ and $^{\chi}P=0.0066$ for PNx vs Control by Sidak's MCT. P<0.0001 for Interactions, P<0.0001 for Pre- vs Post-PNx, and P=0.0079 for PNx vs. Control by nonparametric 2-Way repeated measures ANOVA (NP 2-Way RM ANOVA). For VE: $^{a}P<0.0001$ vs. Pre1-3 by Tukey's multiple comparison test (MCT), $^{\alpha}P=0.0002$, $^{\beta}P=0.0001$ and $^{\chi}P=0.0001$ for PNx vs Control by Sidak's MCT. P<0.0001 for Interactions, P<0.0001 for Pre- vs Post-PNx, and P=0.0005 for PNx vs. Control by NP 2-Way RM ANOVA.
Figure 4:
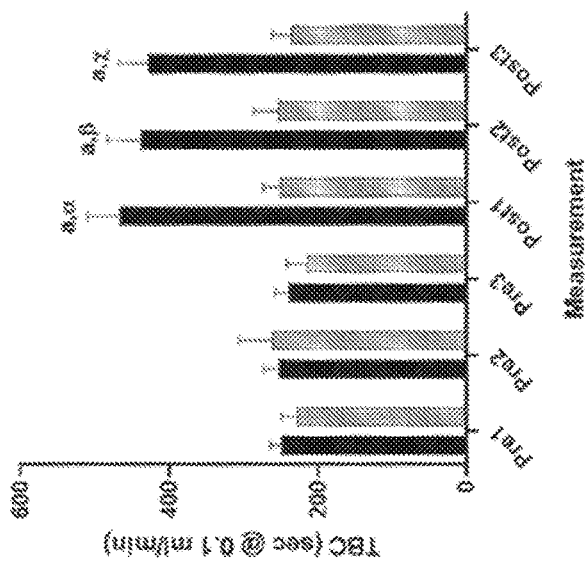

In phase one, reliable and consistent bladder contractions were observed in response to PUES. FIG. 2 is a representative cystometrogram at stable bladder volume with associated scoring of responses to 20-50V, 20 Hz PUES trials. Overall positive responses were observed at 20 Hz (0-86% success across V) and 50 Hz (0-75% success across V) (FIG. 3). The success rate of PUES was significantly greater at 40 and 50V compared to 10k -30V (P<0.0001). There were no significant differences seen between 20 and 50 Hz at any voltage.

Duke University and Durham Veteran Affairs Medical Center Institutional Animal Care and Use Committees approved this study, and all experiments were performed at the Durham Veteran Affairs Medical Center. Rats were housed with 12:12-h light-dark cycles, 72° F. with food and water available ad libitum.

Example 2

In phase two, twenty-five urethane-anesthetized adult female Sprague-Dawley rats underwent the same surgical preparation up to electrode placement. Because regular gross oscillations of the urethra during PUES-induced bladder contractions were visually observed in some non-voiding and all voiding contractions in phase one, reminiscent of phasic electromyographic and pressure recordings associated with voiding (6-10 Hz), it was reasoned that the electrode overlay may have mechanically obstructed the urethra. Therefore, an electrode-bearing thin flexible electrode support was developed for anatomical placement similar to a mid-urethral sling. Use of pubic symphysectomy was continued for experimental purposes because of ease of access. Following symphysectomy, the urethra was carefully hydrodissected from the vagina and a 3 mm-wide thin flexible electrode support (fiberglass screen; Clear Advantage; New York Wire, Grand Island, NY) with integrated 50 µm diameter Teflon-coated bipolar electrodes was placed between the proximal urethra and vagina (FIG. 1B, right). The right pelvic nerve was also exposed and marked for future PNx. Following 3 hours of continuous cystometry, 3 single-fill cystometrograms were performed prior to PNx (8 of 25 rats served as sham PNx controls). Subsequently, all animals underwent 1 hour of continuous cystometry, and 3 single-fill cystometrograms were again performed.

In PNx rats, the bladder was then filled to the largest pre-PNx TBC or 75% of lowest post-PNx TBC (the lower of two volumes was tested first) and PUES was performed at 20, 30, 40, and 50 Hz (varied randomly) at 50V for 60 s on/120 s off between stimulations. Because no lower extremity somatomotor activity was observed with stimulation, tests were performed at 50V. PUES was then repeated at the higher of the two test volumes. When voiding occurred, bladders were emptied and refilled to the test volumes. Residual volumes were recorded during emptying. Measurements included TBC and voiding efficiency (VE; residual volume/(residual volume+TBC)) of spontaneous voiding contractions before and after PNx, the presence or absence of voiding and non-voiding bladder contractions evoked by PUES, and VE of the former. Data were analyzed using non-parametric repeated measures 2-Way ANOVA for sham PNx vs PNx comparisons of TBC and VE, and contingency analysis (CA) for comparisons of different test fill volumes, and sequence and frequency of PUES.

Figure 5:
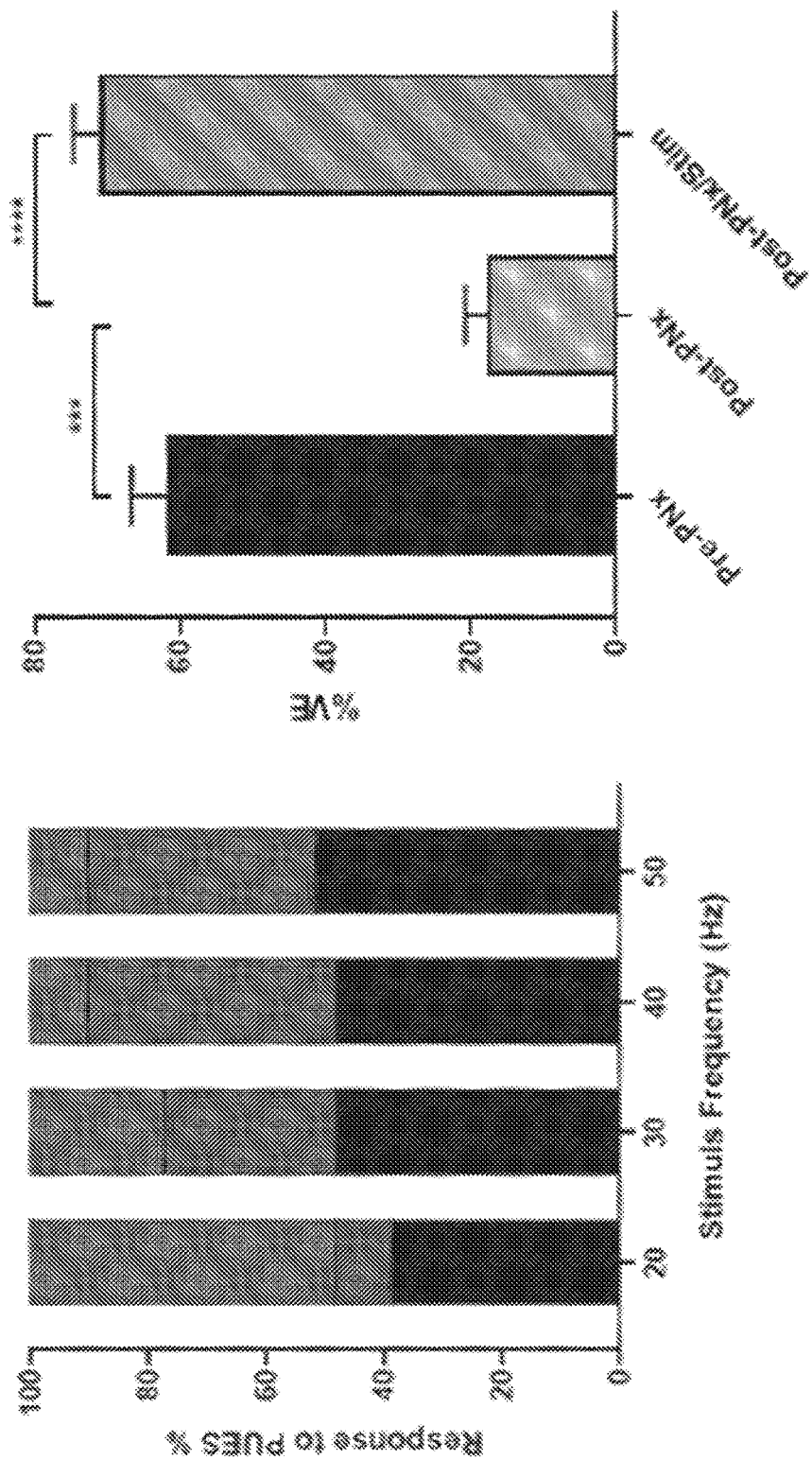
FIG. 5: Proportional responses to PUES after right pelvic nerve transection (left panel; n=31 trials for each stimulus frequency). Red=voiding contraction; Blue=Non-voiding Contraction; Black=No Response. Average voiding efficiency (from left-to-right) for pre-PNx single-fill cystometrograms, post-PNx cystometrograms, and when voiding contractions were present from PUES (right panel; n=14 across all conditions). It is important to note that 60-70% VE is normal for urethane anesthetized rats with open abdomens. P<0.0001 by Friedman Test, * P<0.001 and ** P<0.0001 by Dunn's MCT.

In phase two experiments, PUES was applied to the dorsal urethral surface, including immediate periurethral tissue, using a thin, flexible fiberglass mesh support (FIG. 1B, right). When PUES was applied after right-sided PNx at either the largest pre-PNx bladder capacity or 75% of the lowest Post-PNx bladder capacity, substantial improvements in voiding function were observed (FIG. 5). The selected lower bladder capacities were for PUES after PNx for two reasons: first, pre-PNx bladder capacity was considered to be normal, so normalization of voiding function was anticipated using stimulation; second, attempts were made to avoid false positive spontaneous bladder contractions, which might be present if the new post-PNx bladder capacity were approached. It was acknowledged that not every stimulation (even at the most successful frequency, 20 Hz) resulted in a void or even a contraction. This may be attributed to the preparation, changes in electrode resistance in vivo, or potentially dampening vs. additive effects from repeated stimulations. As stimulation frequencies were randomized, the effect of frequency order on bladder response was able to be assessed, and no significant effect was noted. Still, at 20 Hz (50 V), 61% of stimulations resulted in a contraction and 84% of these resulted in a void (FIG. 5, left panel). What is most exciting is that when the rats voided, their voiding efficiency returned to that of the pre-PNx state (FIG. 5, right panel), essentially reversing the pathological effects of unilateral PNx.

In both experimental phases, cystometric data were collected using a PowerLab 8/35 and Lab-Chart Pro 8.0 (ADInstruments, Colorado Springs, CO). All statistical analyses were performed using GraphPad Prism (version 8.1.2 (322), GraphPad Software, La Jolla, Calif.) or JMP Pro (version 14.0.0, Cary, NC).

What is claimed is:

1. A method of treating underactive bladder in a subject, the method comprising:
   manipulating a controller to provide input associated with inducement of at least one physiological response to a pulse generator, wherein the pulse generator is configured to generate a plurality of pulses based on the input, and wherein a plurality of electrodes is functionally coupled to the pulse generator;
   placing the plurality of electrodes orthogonally across and in contact with a dorsal extraluminal surface of the subject's proximal urethra whereby the plurality of electrodes is positioned to simultaneously stimulate the subject's pelvic, hypogastric, and pudendal nerves bilaterally, wherein the plurality of electrodes is configured to be spaced from 0.1 cm to 2.0 cm apart and comprises a flexible electrode support; and
   activating the pulse generator to cause the plurality of pulses to be delivered from the plurality of electrodes;
   wherein activation of the pulse generator simultaneously stimulates the subject's pelvic, hypogastric, and pudendal nerves and induces the at least one physiological response in the subject, wherein the at least one physiological response comprises at least one of bladder voidance contractions, voiding-associated rhabdosphincter relaxation, and urethral circumferential smooth muscle relaxation, whereby at least one symptom associated with underactive bladder in the subject is improved.

2. The method according to claim 1, wherein the subject has been diagnosed with Detrusor Underactivity (DU).

3. The method according to claim 1, wherein the at least one physiological response in the subject also comprises Barrington's Reflex 2, 4, and/or 7.

4. The method according to claim 1, wherein manipulating the controller comprises selecting pre-determined input parameters associated with the at least one physiological response.

5. The method according to claim 4, wherein the predetermined input parameters comprise one or more of pulse frequency, voltage, duration, amplitude and/or pattern.

6. The method according to claim 1, wherein the method improves at least one symptom associated with underactive bladder in the subject.

7. A method of treating underactive bladder in a subject, the method comprising:
   manipulating a controller to provide input associated with inducement of at least one physiological response to a pulse generator, wherein the pulse generator is configured to generate a plurality of pulses based on the input, and wherein a plurality of electrodes is functionally coupled to the pulse generator;
   placing the plurality of electrodes orthogonally across and in contact with a dorsal extraluminal surface of the subject's proximal urethra whereby the plurality of electrodes is positioned to simultaneously stimulate the subject's pelvic, hypogastric, and pudendal nerves bilaterally; and activating the pulse generator to cause the plurality of pulses to be delivered from the plurality of electrodes;

wherein activation of the pulse generator simultaneously stimulates the subject's pelvic, hypogastric, and pudendal nerves and induces the at least one physiological response in the subject, wherein the at least one physiological response comprises at least one of bladder voidance contractions, voiding-associated rhabdosphincter relaxation, and urethral circumferential smooth muscle relaxation, whereby at least one symptom associated with underactive bladder in the subject is improved.

8. The method according to claim 7, wherein the subject has been diagnosed with Detrusor Underactivity (DU).

9. The method according to claim 7, wherein the at least one physiological response in the subject also comprises Barrington's Reflex 2, 4, and/or 7.

10. The method according to claim 7, wherein manipulating the controller comprises selecting pre-determined input parameters associated with the at least one physiological response.

11. The method according to claim 10, wherein the pre-determined input parameters comprise one or more of pulse frequency, voltage, duration, amplitude and/or pattern.

12. The method according to claim 7, wherein the method improves at least one symptom associated with underactive bladder in the subject.

* * * * *